United States Patent [19]
Macovski et al.

[11] 4,413,353
[45] Nov. 1, 1983

[54] X-RAY ENCODING SYSTEM USING AN OPTICAL GRATING

[76] Inventors: Albert Macovski, 2505 Alpine Rd., Menlo Park, Calif. 94025; Bruno Strul, 2633 Waverley St., Palo Alto, Calif. 94306; Robert E. Alvarez, 2369 Laura La., Mountain View, Calif. 94043

[21] Appl. No.: 299,208

[22] Filed: Sep. 3, 1981

[51] Int. Cl.³ .................... A61B 6/00; G01N 23/04; G03B 41/16; H04N 5/32
[52] U.S. Cl. .............................. 378/062; 378/2
[58] Field of Search .................. 378/164, 2, 41, 62

[56] References Cited
U.S. PATENT DOCUMENTS

| | | | |
|---|---|---|---|
| 2,344,823 | 3/1944 | Landis et al. | 378/164 |
| 2,344,824 | 3/1944 | Landis et al. | 378/164 |
| 3,382,362 | 5/1968 | Tokuyama et al. | 378/41 |
| 3,499,150 | 3/1970 | Tajima et al. | 378/62 |
| 3,783,282 | 1/1974 | Hoppenstein | 378/41 |

OTHER PUBLICATIONS

Flader, L. "Photoengraving", *Encyclopedia Americana*, Americana Corp., 1978, pp. 798c–798d.

*Primary Examiner*—Alfred E. Smith
*Assistant Examiner*—T. N. Grigsby
*Attorney, Agent, or Firm*—John L. McGannon

[57] ABSTRACT

X-ray information is encoded onto photographic film by placing an optical grating between the light-emitting scintillating screen and the photographic emulsion. Information at different energies is encoded by displacing the grating between exposures or by using static gratings with an energy-selective dual screen.

26 Claims, 7 Drawing Figures

X-RAY ENCODING SYSTEM USING AN OPTICAL GRATING

BACKGROUND OF THE INVENTION

1. Field of the Invention

This invention relates to radiography. In a primary application the invention relates to the encoding of information representing different x-ray energies onto photographic film where the decoded information is used to selectively image specific materials.

2. Description of the Prior Art

Conventional radiography records the transmission through the body over a broad spectrum of x-ray photon energies. This integration over the energy spectra results in a superposition of all tissues and materials in the final image making it different to visualize many structures of interest. For example, tumors and other soft tissue lesions are often obscured by bone. Also, large amounts of iodine must be administered to blood vessels, in highly invasive procedures, to make them visible in the presence of other tissues.

Different materials have attenuation coefficients which have unique functions of energy. By making measurements at different regions of the energy spectrum, and combining them in appropriate data-processing systems, specific materials can be removed or isolated. A general system with this capability is described in U.S. Pat. No. 3,848,130, "Selective Material X-Ray Imaging System," issued to A. Macovski. Here the measurements made at various energy spectra are combined to make images representing different materials. In this patent, however, the images of the various measurements made separately and in sequence. As a result, a registration problem exists when the various images are combined.

The registration problem is solved by the system described in U.S. Pat. No. 3,950,613, "X-Ray Encoding and Decoding System," issued to A. Macovski. In this patent the x-ray energy information is encoded on a single film in the form of repetitive grating patterns. These grating patterns are formed by x-ray absorbing gratings which are placed between the x-ray source and film-screen cassette. Although this solves the registration problem by placing all the measurement images on a single film, it introduces resolution problems. The x-ray encoding gratings must have relatively low spatial frequencies in order to be adequately resolved by the scintillating screen. The information encoded using this low-frequency grating has relatively poor resolution. In addition, x-ray encoding gratings are difficult to fabricate and, in some configuration, necessitate additional radiation dose to the patient.

A preferred approach to the use of energy-selective information in radiography is described in U.S. Pat. No. 4,029,963, "X-Ray Spectral Decomposition Imaging System," issued to R. E. Alvarez and A. Macovski. Here measurements are made at two regions in the x-ray energy spectrum, with the measurements processed to form the photoelectric and Compton scattering components of the materials. These components, representing essentially atomic number and density, can be combined to represent different materials. This patent described both the CT and projection radiography applications of selective energy imaging.

In the projection system a single-exposure system is described using an energy-selective dual-cassette detector where the lower energies are absorbed primarily in the front screen and the higher energies in the back screen. These resultant images are recorded selectively on a single color film by having the front and back screens produce different colors. These are then scanned to provide the desired low-energy and high-energy information. The use of color film, however, presents significant difficulties. The film is both expensive and less sensitive than black and white film. Also, the use of screens emitting different colors restricts the choice of optimum screen material.

SUMMARY OF THE INVENTION

An object of this invention is to provide a method of encoding x-ray information onto photographic film without restricting the resolution. It is a further object of this invention to provide a means of encoding x-ray energy information onto photographic film to provide high-resolution images of specific materials.

It is a further object of this invention to provide an effective encoding system for recording x-ray images taken at different times for use in subtraction radiography.

Briefly, in accordance with the invention, an optical grating is placed between the scintillating screen and the photographic emulsion. In the sequential mode a measurement is made at a first energy spectrum with the grating in the initial position. A measurement is then made at a second energy spectrum with the grating translated. In the simultaneous mode the gratings are used with energy-selective screens to simultaneously record the two energy spectra on the front and back emulsions of a dual-emulsion film. Other x-ray information, such as temporal changes, can also be recorded using the encoding grating.

DESCRIPTION OF THE PREFERRED EMBODIMENT

Figure 1:
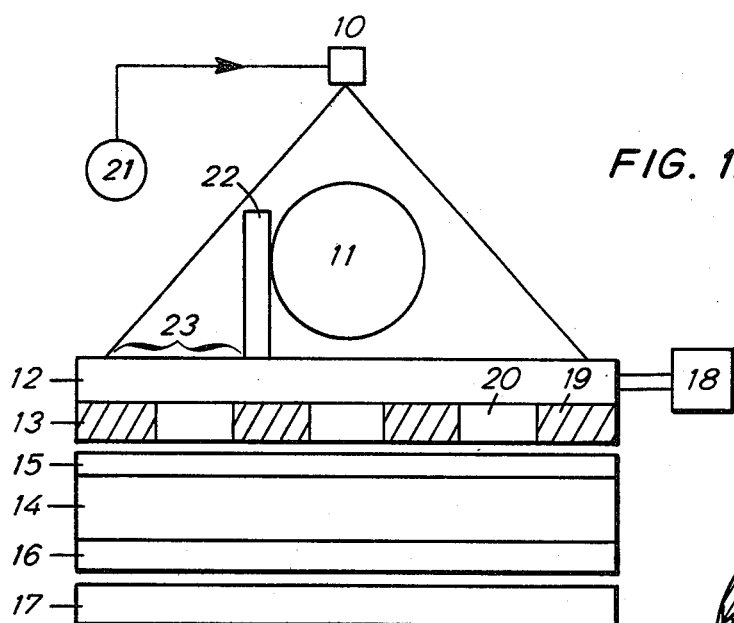
FIG. 1 is a schematic illustrating an embodiment of the invention.

An understanding of the broad aspects of the invention may best be had by reference to FIG. 1. Here it is desired to encode various radiographic characteristics of object 11 onto photographic film 14. X-ray source 10, an x-ray tube powered by generator 21, projects an x-ray beam through object 11, usually the anatomy of a patient undergoing a radiographic study. The transmitted x-ray image is converted into a light image when the x-rays irradiate scintillating screen 12. The light from screen 12 creates a latent image on emulsion 15 of film 14.

In this invention optical grating 13 is placed between screen 12 and emulsion 15 to encode the radiographic information on a high-frequency spatial carrier. This is similar to the system described in previously referenced Patent U.S. Pat. No. 3,950,613. In that patent an x-ray grating rather than an optical grating was used to produce the encoded grating pattern on the screen itself. In that system the screen is required to resolve the grating frequency. Since the resolving capability of screens are relatively low, usually under 10 line pairs per mm, the resulting system resolution is correspondingly low. In this invention, however, the screen need not resolve the grating pattern. Only film emulsion 15 is required to resolve the high frequency grating pattern. Film emulsions characteristically can resolve about an order of magnitude higher spatial frequencies than screens.

Figure 2:
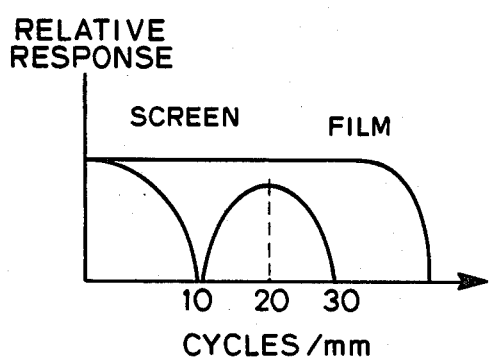
FIG. 2 is a graph describing the performance of the invention.

The resultant spatial frequency spectra in cycles per mm is illustrated in FIG. 2. Here the optical grating is at 20 cycles or line pairs per mm. It is placed in the spectral region beyond that of the screen bandwidth so that the film can separately record a low-frequency image and a modulated image. In the prior art, using an x-ray grating, the low-frequency and modulated images would all fit within the screen bandwidth, forcing reduced resolution.

Returning to FIG. 1, optical grating 13 has alternate opaque and transparent strips such as opaque strip 19 and transparent strip 20. This grating can be formed by simply painting an array of opaque lines onto screen 12. A dual-emulsion dual-screen system is shown which is the type conventionally used in a film-screen cassette. It includes screens 12 and 17 and emulsions 15 and 16. A single optical grating 13 is shown. This is adequate for encoding onto emulsion 15. An additional optical grating can be placed between screen 17 and emulsion 16 to encode on both emulsions. In this embodiment, these gratings would be identical since they are encoding the same information.

The system, as described, simply encoded the x-ray transmission through object 10. The major strength of this approach, however, lies in the ability to encode more than one image on film 14. For example, in U.S. Pat. No. 3,950,613 the transmission at various x-ray energy spectra were encoded using the x-ray grating. These were then decoded to provide image of specific materials. These images are of profound use in the diagnosis of disease.

Energy information can be encoded in the system of FIG. 1. A first encoded image is formed with generator 21 at a specific voltage, resulting in a specific energy spectrum emitted from x-ray source 10. This is used to encode the information on emulsion 15 through optical grating 13 as previously described. Following the exposure generator 21 is switched to a second voltage, providing a second x-ray spectrum. Before the second exposure, grating 13 is translated one-half period normal to the grating lines using mechanical translator 18 so that the positions of the opaque and transparent regions are interchanged. Thus, in the second exposure, the information representing the transmission through object 10 at the second x-ray spectrum is interleaved with that of the first spectrum. In the decoding operation, as described in U.S. Pat. No. 3,950,613, the developed film is scanned providing a high frequency grating signal representing the difference of the two energy spectra, and an average signal, representing the sum of the two spectra.

Translator 18 is shown moving the screen 12 and grating 13. It is only necessary that the grating 13 be translated with respect to the photosensitive surface which is film emulsion 15. Thus translator 18 could move grating 13 along or alternatively could be connected to translate film 14. Since the grid frequency is very high, the movement of the film emulsion 15 by one half period would have a negligible effect on system resolution. It may be more convenient to translate the film than the screen.

Figure 1A:
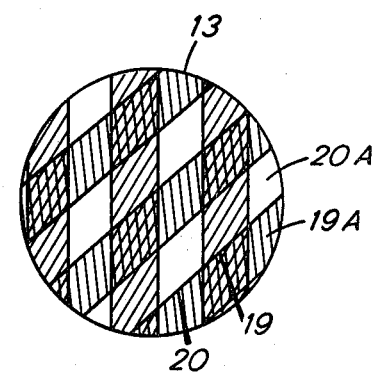
FIG. 1A is an alternate form of this embodiment.

The encoding can take place in a number of ways. For example, grating 13 can be rotated, rather than translated between exposures. In that case 18 would represent a mechanical rotating mechanism rather than a translator. FIG. 1A illustrates the two positions of grating 13 for the case of a circular format. As shown, following the first exposure, grating 13 is rotated so that opaque strip 19 and transparent strip 20 are moved to the positions shown by 19A and 20A respectively. The decoding can be accomplished in a variety of ways. The gratings, when scanned, will provide different electrical frequencies because of the different angles. Alternatively the gratings can be individually decoded by taking advantage of their unique individual spatial frequencies as described in U.S. Pat. No. 3,950,613.

For some studies it is desirable to encode more than two energy spectra. For example, it is often desirable to make an isolated image of a contrast agent with the bone and soft tissue removed. This is the case if vessels are being imaged with an intravenous iodine injection where the vessel cannot be visualized unless the intervening tissue is removed from the image. This can be accomplished by making measurements at three energy spectra, two of which are at either side of the iodine k edge. The encoding of more than two spectra can be accomplished by a variety of combinations of rotating and translating grating 13 into unique positions so that the resultant encoded information can be independently decoded. At each rotation angle, two independent images can be encoded by translation. Although FIG. 1 shows spectral changes resulting from voltage changes on an x-ray tube, this can also be accomplished by x-ray filtering.

Other information, in addition to energy spectra, can be encoded. For example, it is often desired to make x-ray measurements at different times. An example of this is the iodine contrast study previously described. A first image can be made through object 11 before the iodine is injected. Following the injection of the iodine contrast agent, a second image is recorded, using the same energy, with grating 13 translated or rotated as previously described. When the film is scanned, the two decoded signals are subtracted to provide an image of the iodinated vessels only, since all other tissue will cancel out. This procedure is presently done using fluoroscopy with relatively low resolution. The film system with the high-frequency optical grating allows the study to be made at high resolution with a significant improvement in the diagnostic quality. In addition, the film system provides a larger field of view than fluoroscopy.

The decoding of the film during scanning is often aided if a reference signal is available providing a constant amplitude signal of the correct phase and frequency. This can be accomplished if a small region of the film is set aside to record the reference gratings without imaging the object. As shown in FIG. 1, stop 22 is used to prevent the patient 11 from blocking the end of film 14. This allows the x-rays to impinge directly on region 23 of the screen 13 and create a fixed reference pattern. The light from illuminated region 23 passes through grating 13 to form a reference grating pattern on emulsion 15.

Figure 3:
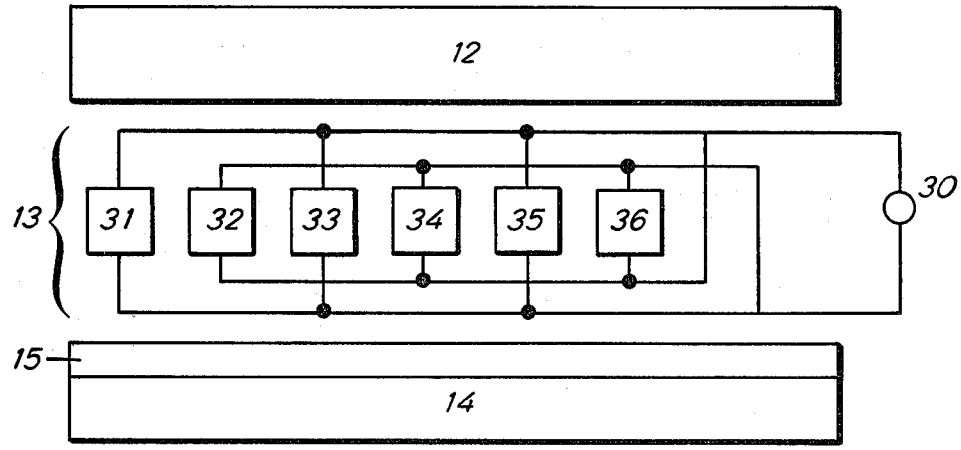
FIG. 3 is another alternate form of the embodiment.

In the systems described thusfar mechanical motion was required to change the grating pattern so as to encode more than one image. Mechanical motion can present problems of accuracy. This can be eliminated using the system of FIG. 3 where the grating is effectively translated electrically. Grating 13 consists of a series of light values driven by voltage source 30 where alternate light values are driven by opposite polarities. At a given polarity of control signal generator 30, for example, valves 31, 33, and 35 will transmit light with valves 32, 34 and 36 opaque. A first exposure is made of a first image onto screen 12 providing an encoded latent image on emulsion 15 of film 14. Following this exposure the polarity of control signal generator 30 is reversed making valves 31, 33 and 35 opaque and 32, 34 and 36 transmissive. This effectively translates the grating by one-half period. A second exposure is then made using a second image as previously described.

A variety of light valves can be used, such as liquid crystals. Also electro-optic crystals can be used which effectively cause a change in the polarization of the light. In that case the array of valves, grating 13, is sandwiched by crossed linear polarizing material. For many light valves the desired change from opaque to transparent will require voltage changes other than the change in polarity shown in the example.

In the system described thusfar, the images at different x-ray spectra were recorded in sequence. These systems suffer from the possibility of undesired patient motion between exposures. This problem was solved by the method described in the previously referenced Patent U.S. Pat. No. 4,029,963. Here information on two energy spectra was recorded simultaneously using energy-selective detection. Since lower energies interact primarily in the first scintillating screen 12, and higher energies in the second scintillating screen 17, if these are individually recorded, simultaneous energy-selective imaging can be accomplished. In U.S. Pat. No. 4,029,963 this was accomplished with color film with its previously-mentioned difficulties. This can be much better accomplished, as shown in FIG. 4, using the inventive principle of the optical encoding grating between the screen and the film emulsion.

Figure 4:
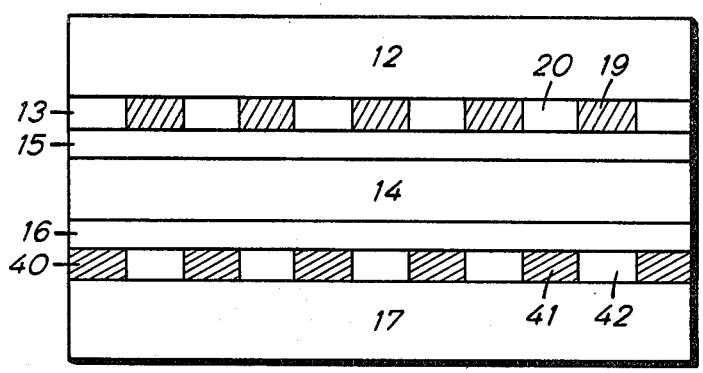
FIG. 4 is a schematic illustrating a second embodiment of the invention using energy selective detection.
Figure 4A:
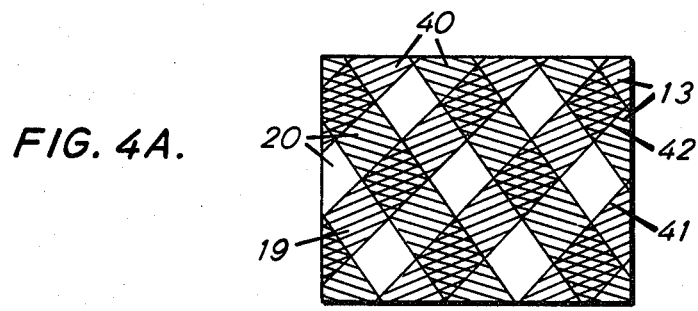
FIG. 4A is an alternate form of the second embodiment.

As shown in FIG. 4, grating 13 is between screen 12 and emulsion 15 and grating 40 is between screen 17 and emulsion 16. Grating 40 can, as shown, be of the same frequency but of opposite polarity to grating 13. Here opaque strip 41 and transparent strip 42 are opposite transparent strip 20 and opaque strip 19 respectively. The resultant encoded pattern can be decoded as previously described. Alternatively grating 40 can be at a different periodicity and/or different angle than that of grating 13. This is illustrated in FIG. 4A showing the superimposition of gratings 13 and 40 as they would appear on an encoded image. In grating 13 strips 19 and 20 are at one angle while those of grating 40 are at an equal and opposite angle with respect to the vertical. This method of encoding is employed in existing color television cameras. One method of decoding the resultant encoded pattern is to make use of the phase shift of the grating signal on alternate lines. One signal will experience a phase increase while the other experiences a phase decreases. Thus, by simultaneously viewing adjacent scan lines, the two signals can be separated.

Because of the high frequency nature of gratings 13 and 40, there will essentially be no cross-talk from each grating image to the opposite emulsion. Each modulated high frequency light image will be defocused at the opposite emulsion. Any semblance of cross-talk can be eliminated, however, by making the film base of film 14 opaque to the light emitted from screens 12 and 17. Thus the base should be opaque at the color corresponding to the light from the screens. When the developed film is scanned, however, the scanning light is chosen to be a color transmitted by the film base.

Although FIG. 4 shows two gratings, the system will work well with a single grating. Thus, for example, grating 40 can be eliminated. In that case the low-energy information from screen 12 is encoded on emulsion 15 through grating 13. The high-energy information from screen 17 is recorded on emulsion 16 solely as a low-frequency baseband image without a modulated carrier. When the developed film is scanned, the low-frequency baseband signal represents both the low and high energy information while the high frequency grating signal represents just the low energy information. By decoding the grating signal to find the low-energy signal, it can then be subtracted from the baseband signal to isolate the high-energy information.

In addition to providing improved resolution, the various systems described thusfar will also provide dose reduction as compared to the x-ray gratings shown in the prior art. These gratings reduced the x-rays reaching the screen, thus requiring additional dose. Using optical gratings, all of the x-rays are allowed to reach the screens.

Figure 5:
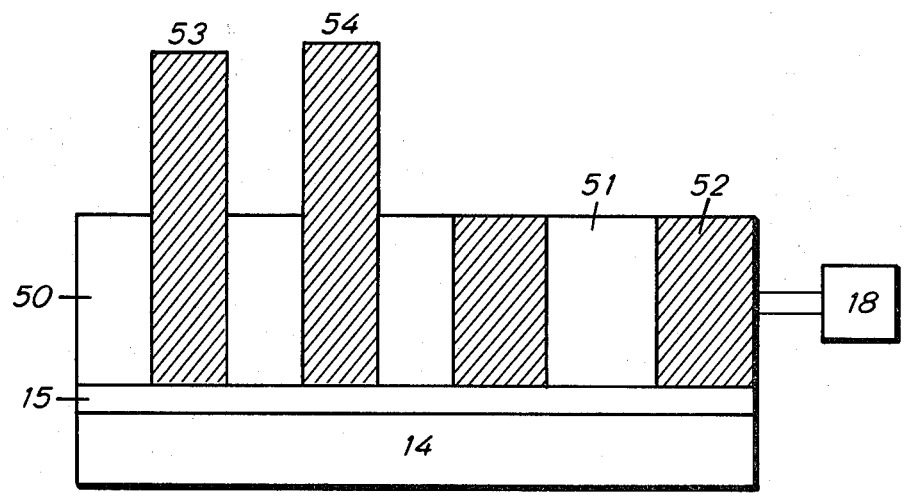
FIG. 5 is a schematic illustrating a third embodiment.

The system illustrated in FIG. 5 provides x-ray scatter reduction in addition to multiple-image encoding. A grating 50 is formed with alternate optically opaque material 52 and screen material 51. The x-rays thus cause scintillations in the screen material only, resulting in an encoded pattern on emulsion 15 of film 14. To record two x-ray images grating 50 is translated between exposures using translator 18. Alternatively grating 50 can be rotated to record multiple images as previously described.

The grating is high resolution since the confined phosphor material 51 prevents the usual light spreading. For improved collection efficiency the sides of phosphor strips 51 can be made reflective so as to collect the light which hits the opaque strips 52.

If opaque strips 52 are made metallic and relatively opaque to x-rays also, such as the use of lead strips, grating 50 will serve the additional function of scatter suppression. Scattered x-rays arriving at the grid at angles other than substantially normal to the image plane will tend to be absorbed by the metallic strips if they pass through the screen material. The scatter reduction can be enhanced by making the opaque strips deeper than the phosphor strips as illustrated by strips 53 and 54.

Although the invention was described using photographic film, clearly a wide variety of photosensitive surfaces can be used other than photographic emulsions. These can include, photoconductive surfaces such as are used in photocopy machines, photocathodes of image intensifiers and television cameras and a wide variety of non-silver light-sensitive materials.

What is claimed:

1. In a method for encoding x-ray information onto a photosensitive surface for subsequent decoding with a scanning operation using the light from a scintillating screen the steps of:

irradiating the screen with an x-ray image; and interrupting the light from the screen reaching the photosensitive surface using a repetitive series of parallel optically opaque lines forming a one dimensional grating pattern where the width of opaque lines is substantially equal to the distance between the opaque lines.

2. The method as described in claim 1 including the steps of:
   translating the repetitive series of lines with respect to the photosensitive surface; and
   irradiating the screen with a second x-ray image.

3. The method as described in claim 1 including the step of irradiating a second screen with the x-rays which have passed through the first screen.

4. The method as described in claim 3 including the step of recording the light from the second screen on a second photosensitive surface.

5. The method as described in claim 4 including the step of interrupting the light from the second screen reaching the second photosensitive surface using a second repetitive series of optically opaque lines different than that of the first repetitive series.

6. Apparatus for encoding x-ray image onto a photosensitive surface for subsequent decoding with a scanning operation comprising:
   a scintillating screen which converts the impinging x-ray image information into a light image; and
   a one-dimensional optical grating having opaque and transparent parallel strips of substantially equal width placed between the scintillating screen and the photosensitive surface whereby the x-ray image is encoded as modulations of the grating pattern.

7. Apparatus as described in claim 6 wherein a second x-ray image is encoded in addition to the first x-ray image including means for irradiating the screen with a second x-ray image and means for translating the optical grating with respect to the photosensitive surface between the first and second image exposure such that the positions of the opaque and transparent regions are substantially interchanged.

8. Apparatus as described in claim 7 wherein the means for translating the optical grating with respect to the photosensitive surface includes means for translating the photosensitive surface with respect to a stationary grating.

9. Apparatus as described in claim 6 wherein a second x-ray image is encoded in addition to the first x-ray image including means for irradiating the screen with a second x-ray image and means for rotating the optical grating with respect to the photosensitive surface between the first and second image exposures.

10. Apparatus as described in claim 6 wherein the optical grating consists of electro-optical material where the opaque and transparent regions can be interchanged with a conical signal including means for encoding the first x-ray image with the control signal in a first state and means for subsequently encoding a second x-ray image by irradiating the screen with the second x-ray image with the control signal in a second state having the opaque and transparent regions of the grating interchanged with respect to that of the first state.

11. Apparatus as described in claim 6 including means for encoding a plurality of x-ray images including means for sequentially irradiating the screen with each of the plurality of x-ray images and means for repositioning the grating to a different position between each image exposure.

12. Apparatus as described in claims 7,9 or 10 wherein the first x-ray image represents the x-ray transmission at a first energy spectrum and the second x-ray image represents the x-ray transmission at a second energy spectrum.

13. Apparatus as described in claims 7, 9 or 10 wherein the first x-ray image represents the x-ray transmission at a first time interval and the second x-ray image represents the x-ray transmission at a second time interval.

14. Apparatus as described in claim 6 for simultaneously encoding two x-ray images representing the x-ray transmission at two x-ray spectra including a second scintillating screen receiving the x-rays transmitted by the first scintillating screen.

15. Apparatus as described in claim 14 including a second photosensitive surface and a second optical grating different than the first optical grating placed between the second scintillating screen and the second photosensitive surface.

16. Apparatus as described in claim 15 wherein the second optical grating is parallel to that of the first grating with the relative positions of the opaque and transparent regions interchanged.

17. Apparatus as described in claim 15 wherein the second optical grating has a different periodicity than that of the first optical grating.

18. Apparatus as described in claim 15 wherein the lines of the second optical grating are at a different angle than those of the first optical grating.

19. Apparatus as described in claims 14 or 15 including a layer opaque to the light from the scintillating screens between the first and second screens.

20. Apparatus as described in claims 6, 11, 14 or 15 including means for recording reference grating patterns identical to those of the encoding optical gratings on a non-imaging region of the photosensitive surface.

21. Apparatus as recited in claims 6, 11, 14 or 15 wherein the frequency of the optical grating is greater than the highest frequency which can be substantially resolved by the screen.

22. Apparatus as recited in claim 21 where the frequency of the optical grating is greater than 10 line pairs per millimeter.

23. Apparatus for encoding an x-ray image onto a photosensitive surface for subsequent decoding with a scanning operation comprising:
   a one-dimensional grating screen consisting of a repetitive line pattern of scintillating material with optically opaque material between the lines of scintillating material with the width of the opaque material being substantially equal to the width of the scintillating material which converts the impinging x-ray image into a modulated light image; and
   a photosensitive surface in substantial contact with the grating screen.

24. Apparatus as described in claim 23 where the optically opaque material is also substantially opaque to x-rays whereby scattered radiation is reduced.

25. Apparatus as described in claims 23 or 24 including a second x-ray image provided in sequence after the first x-ray image and means for translating the grating screen between the irradiation of the grating screen with the first and second x-ray images such that the positions of the opaque and scintillating regions are substantially interchanged.

26. Apparatus for encoding x-ray images for subsequent decoding with a scanning operation representing two energy spectra comprising;
   a first scintillating screen which absorbs primarily in the lower energy region of the incident x-ray spectrum;

a first photosensitive surface which receives the light from the first scintillating screen;

a second scintillating screen which receives the x-rays transmitted by the first scintillating screen;

a second photosensitive surface between the first photosensitive surface and the second scintillating screen which receives light from the second scintillating screen; and an optical grating immovably positioned between either scintillating screen and its corresponding photosensitive surface having an array of alternate opaque and transparent strips where the widths of the opaque and transparent strips are substantially equal.

* * * * *

UNITED STATES PATENT AND TRADEMARK OFFICE
CERTIFICATE OF CORRECTION

PATENT NO. : 4,413,353

DATED : November 1, 1983

INVENTOR(S) : Macovski, et al.

It is certified that error appears in the above-identified patent and that said Letters Patent is hereby corrected as shown below:

At column 1, line 4, insert --This invention was made with Government support under Contract No. NAS5-25043 awarded by the National Aeronautics and Space Administration. The Government has certain rights in this invention.--

Signed and Sealed this

Fourth Day of April, 1995

Attest:

BRUCE LEHMAN

Attesting Officer

Commissioner of Patents and Trademarks